United States Patent
Draenert

[19]
[11] Patent Number: 5,824,083
[45] Date of Patent: *Oct. 20, 1998

[54] CEMENT-FREE FEMORAL PROSTHESIS COMPONENT AND METHOD OF PRODUCING IT

[76] Inventor: Klaus Draenert, Gabriel-Max-Str. 3, D-8000 München 80, Germany

[ * ] Notice: The term of this patent shall not extend beyond the expiration date of Pat. No. 5,554,190.

[21] Appl. No.: 356,286
[22] PCT Filed: Apr. 26, 1993
[86] PCT No.: PCT/EP93/01003
   § 371 Date: Oct. 21, 1994
   § 102(e) Date: Oct. 21, 1994
[87] PCT Pub. No.: WO93/21864
   PCT Pub. Date: Nov. 11, 1993

[30] Foreign Application Priority Data

Apr. 24, 1993 [DE] Germany ............... 42 13 598.2

[51] Int. Cl.⁶ ........................................... A61F 2/28
[52] U.S. Cl. ...................... 623/16; 623/901; 623/22
[58] Field of Search ................ 623/16, 18, 22, 623/66, 901

[56] References Cited

U.S. PATENT DOCUMENTS

| | | |
|---|---|---|
| 3,893,196 | 7/1975 | Hochman . |
| 4,936,862 | 6/1990 | Walker et al. ............... 623/18 |
| 5,037,442 | 8/1991 | Wintermantel et al. ........... 623/23 |
| 5,086,401 | 2/1992 | Glassman et al. .............. 395/94 |
| 5,274,565 | 12/1993 | Reuben ...................... 623/16 |
| 5,306,306 | 4/1994 | Bisek et al. ................. 623/16 |
| 5,343,385 | 8/1994 | Joskowicz et al. .......... 364/167.01 |
| 5,360,446 | 11/1994 | Kennedy ..................... 623/16 |
| 5,365,996 | 11/1994 | Crook ....................... 164/45 |
| 5,370,692 | 12/1994 | Fink et al. .................. 623/16 |
| 5,397,365 | 3/1995 | Trentacosta ................. 623/16 |

FOREIGN PATENT DOCUMENTS

| | | |
|---|---|---|
| 0255797 | 2/1988 | European Pat. Off. ........... 623/16 |
| 0358601 | 3/1990 | European Pat. Off. ........... 623/16 |
| 0 479 257 A1 | 4/1992 | European Pat. Off. . |
| WO 89/10730 | 11/1989 | WIPO . |

*Primary Examiner*—John G. Weiss
*Assistant Examiner*—Bruce E. Snow
*Attorney, Agent, or Firm*—Kinney & Lange, P.A.

[57] ABSTRACT

The present invention relates to a femoral prosthesis component for cement-free anchoring and to a method of producing it. The prosthesis component, which can be produced by means of CAD and image-analysis methods, provides for the largest possible surface for the transmission of forces, and its mass and rigidity can be adapted to the individual properties of the bone.

15 Claims, 1 Drawing Sheet

U.S. Patent  Oct. 20, 1998  5,824,083
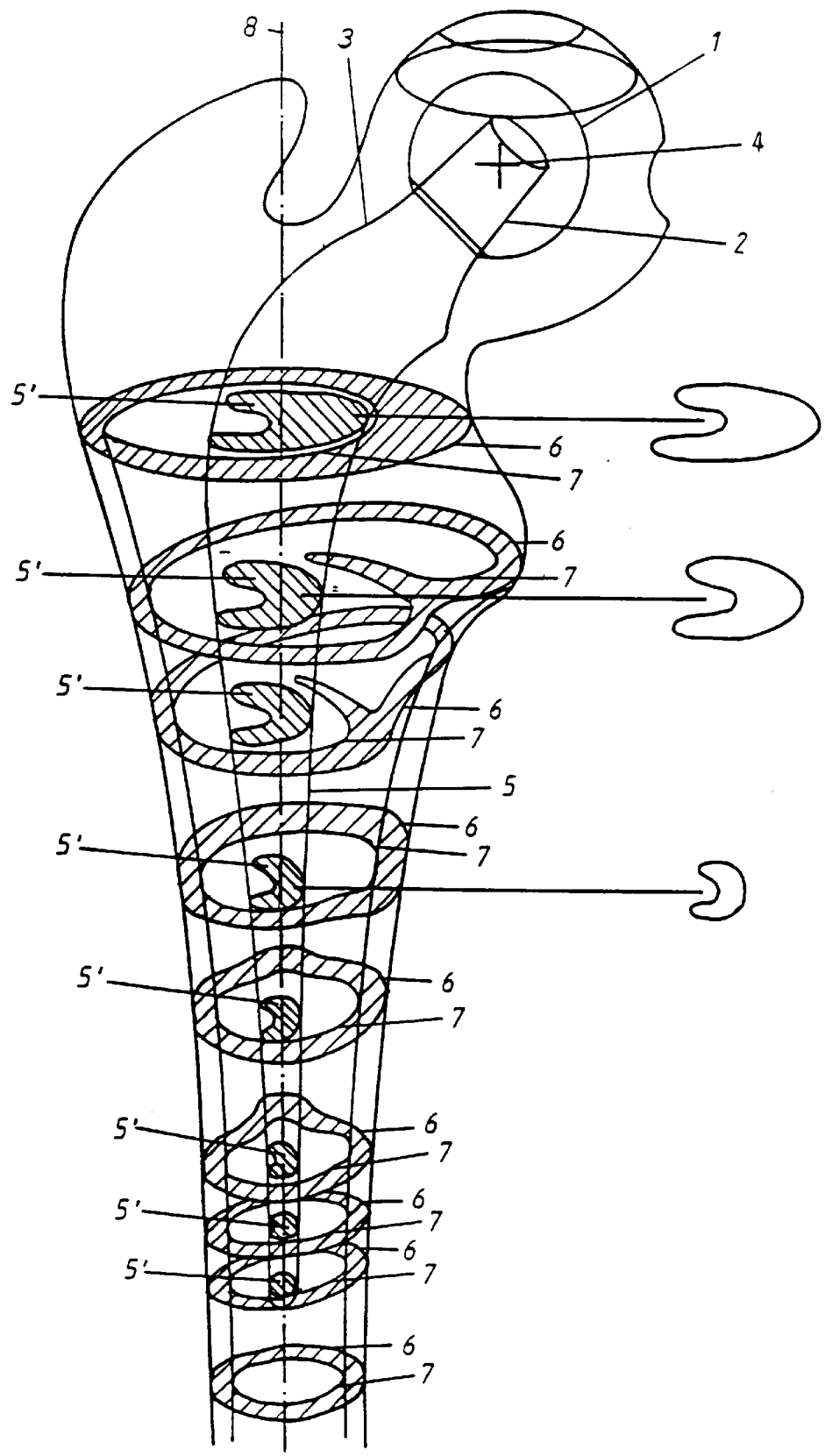

CEMENT-FREE FEMORAL PROSTHESIS COMPONENT AND METHOD OF PRODUCING IT

BACKGROUND OF THE INVENTION

The present invention relates to a femoral prosthesis component which is to be anchored without using cement and a method of producing it.

In the fields of surgery and orthopaedics with respect to the locomotor system, the artificial joint replacement has become a standard surgical intervention and is today one of the most frequently carried out operations of all. The long-term results of replaced joints have been quite variable and the life time of, for example, replaced hip joints ranges from few weeks up to 27 years (Draenert and Draenert 1992).

It has been found out by scientific research that different factors are responsible for the loosening of an endoprosthesis component, such as infections, insufficient surgical skills, choice of the wrong implant and excessive strain. Nevertheless, so far many cases of loosening could not be explained in a satisfying manner. It has only been detected that certain combinations of factors frequently lead to a loosening, such as a massive cement-free implant used in combination with the bone of a rheumatic. Such types of prostheses which were to interlock within the bone and were implanted together with bone cement showed (Draenert 1988) that bone cement as a filling material between metal and bone cannot fulfil an anchoring function but is pulverised.

The problem involved in the anchoring of prosthesis components could in the end be attributed to the phenomenon of bone deformability. This explained why an easily deformable bone of a rheumatic is deformed by a metal prosthesis anchored without cement such that rapid loosening ensued. On the other hand, it could be shown that a fragile or soft spongiosa as well as a normal spongiosa (cancellous bones) can be stiffened by means of polymethylmethacrylate (PMMA) bone cement and thus gets extremely rigid (Draenert and Draenert 1992). A thus stiffened bone structure could be found with all those implants which had successfully been used for 10 to 20 years and could be histologically examined. On the other hand, quite compact femora could be provided with prosthesis components without using bone cement as an anchoring means, and these prosthesis components have successfully been implanted for about 10 years (Draenert and Draenert 1992). However, in these cases, the results could not often be reproduced.

It is an object of the present invention to provide a femoral prosthesis component which can be anchored without using cement and with which, after its implantation, good long-term results can be expected.

SUMMARY OF THE INVENTION

This object is achieved by the present invention.

In connection with the invention, the problem has been investigated how the strength of a bone influences the life time of an implant. By means of histological studies it could clearly be proven that soft, deformable bones only show a stable anchoring if the implants used have a low mass.

The present invention is based on the following findings regarding the anchoring of prostheses: Every bone exhibits an individual shape and an individual strength; therefore, both factors must be taken into account when selecting the prosthesis. A solid, compact bone is a good indication for metal-bone anchoring without using bone cement. Two factors are above all important in this context: 1. to obtain the best possible primary stability of the anchorage and 2. to provide the largest possible surface for the transmission of forces between the prosthesis and the bone. It has, however, to be considered that the various compartments of the bone, such as epiphysis, metaphysis and diaphysis, have completely different shapes and strengths. There were early trials to adapt the prosthesis shaft to the medullary cavity, cf. EP-A-0 038 908; however, it was rapidly found out that one single implant design could not be adjusted to the variety of different bone shapes (Noble et al., 1988); moreover, there was no possibility of determining the strengths of a bone and considering them when designing a prosthesis.

In connection with the present invention, it has been found out that there is a good correlation between the density of a bone and its strength. According to the invention, the density of a bone can therefore be used as a measure for its strength. By combining various image-analysing and computer-aided calculations, a method could be found with which the morphology of the medullary cavity of the bone as well as the strength of the bone could be determined and taken into account for the design of a prosthesis component. These experiments resulted in a design of a prosthesis component which can be fit ideally into the medullary cavity and whose mass and/or stiffness can be selectively changed such that in each case the largest possible surface is provided for the transmission of force between prosthesis and bone.

The mass and/or the stiffness of the femoral prosthesis component according to the present invention can be adjusted to the individual properties of the bone. In the medial, in particular the medioproximal portion of the prosthesis, the bending strength of the prosthesis is the decisive factor. In the lateral portion of the prosthesis, tensile stresses are predominant in the distal as well as in the proximal portion so that there the tensile strength of the prosthesis is also of importance. In the distal portion, the tensile strength is of particular importance. Due to the muscular attachments not covering the neck of the femur and the head of the neck of the femur, there are also torsional forces. In the present invention, the aforementioned properties of the prosthesis material are mostly summarised as "rigidity". According to the present invention, the rigidity of the prosthesis and/or its mass is adapted to the individual properties of the bone.

There are several ways of adaptation; for example, the material of the prosthesis can be selected according to the individual properties of the bone. In case of a dense bone, a material having a higher specific mass and a higher rigidity can be selected whereas in case of a bone with a low density, the material to be selected has a low specific mass and rigidity. CoCrMo alloys, Ti, Ti alloys, steel, plastics or composite materials can for example be used as materials of the prosthesis.

It is also possible to select an inhomogeneous material for the prosthesis component, in the sense that in portions of higher bone density a material of higher specific mass and/or rigidity is used than in portions of lower bone density. In this connection, it has to be considered that the bone density can greatly vary, and that the density of the spongy portion of the bone can be merely 15 to 20% of that of the compact substance of the bone. When using a porous prosthesis material, the desired inhomogeneity of the material can for example be obtained by varying the pore size and reducing it in portions of higher bone density. Composite materials can also be used as material for the prosthesis component wherein, for example, the fibre content of the composite material can vary along the axial length of the prosthesis component. Thus, in particular the rigidity of the prosthesis component can be varied and adapted to the bone density.

Furthermore, the mass and/or the rigidity of the prosthesis component can be adapted to the individual properties of the bone by a suitable selection of the shape of the prosthesis component, particularly of the cross-section of the prosthesis component in various bone portions. If, for example, at least an essential part of the length of the femoral prosthesis component is U-shaped or horseshoe-shaped in its cross-section, as proposed in WO 90/02533, the cross-sectional area and thus the prosthesis mass can be adapted in various sections by a suitable selection of the size and depth of the groove or the slot between the two arms of the U-shaped cross-section. A transition from a solid shaft to a U-shaped cross-section with very thin arms is conceivable according to the invention. The largest possible surface for the transmission of forces between the bone and the prosthesis is guaranteed by the fact that the prosthesis component forms an uninterrupted surface or closed contour in its medial, dorsomedial and anteromedial portions.

The mass and/or the rigidity can for example also be changed, in particular in order to reduce the mass and/or rigidity, by providing bore holes which partly pass through the prosthesis shaft, such as blind holes, or bore holes which completely pass through the prosthesis shaft. On the other hand, ridges and/or reinforcing elements provided at the outer and/or inner contours of the prosthesis, for example of a U-shaped prosthesis shaft, can increase the mass and/or rigidity of the prosthesis component. Such elements can be provided either on portions or over essentially the whole length of the prosthesis component.

The mass and/or the rigidity of the prosthesis component is adapted to the bone density preferably by a linear correlation between the bone density and the mass and/or rigidity of the prosthesis component; that means, for example, that the mass or rigidity of the prosthesis in the respective portion of the prosthesis component is increased proportionally if the bone density is doubled.

In detail, it can be proceeded as follows in order to design and produce such an individual prosthesis component:

A patient having a deformed hip joint changed due to arthrosis is examined in a CT scanner, and stacked images of both hip joints are digitized and stored as cross-sectional images. So-called binary images are produced of the cross-sectional images by means of image analytical methods, i.e. black and white contrast images whose inner and outer contours can be analysed and which depict the femur. The inner contour is put together in a 3D model. The centre of rotation of the hip joint is determined and depicted as the centre of a sphere together with the contour model by means of the image analysis (cf. FIGURE).

The shape of the shaft of the prosthesis component can subsequently be adapted to the shape of the medullary cavity. By means of several, for example six to ten, preferably nine sections which are evenly distributed along the length of the proximal femur, the density per unit area of the bone is determined via the binary image and compared with the corresponding section of a normal femur which has been previously analysed. This comparison results in a correlation factor as a measure of the strength of the individual bone, on the basis of which the ratio between the cross-section of the prosthesis and that of the medullary cavity can be determined. If the specific bone density corresponds to that of the normal femur, the contour model of the medullary cavity is eccentrically and/or concentrically reduced by 1 to 20%, preferably by 5 to 10%, in order to determine the cross-section of the prosthesis component in the respective section. If the specific bone density is lower than that of the normal femur, the contour model is correspondingly more reduced to determine the cross-section of the prosthesis. The values between the individual sections can be interpolated. The set of data of the contour model is transferred together with the position of the centre of rotation to a CAD unit. In the CAD unit, the axis of the contour model is determined and undercuts in the design are corrected such that the prosthesis component can be inserted in a press fit manner into the medullary cavity with a rectilinear movement and/or with a slight screwing movement. The design such obtained is retransferred to the image-analysis unit in which a double contour model of the outer and the inner contours of the femur is produced, into which the prosthesis component can be fitted. Finally, while considering and correcting the enlargement ratio, the prosthesis component is projected into the ap X-ray image (path of the rays anterior-posterior) and the axial X-ray image, and inserted along its implantation axis. The mass and/or rigidity of the prosthesis is determined to be proportional to the bone density. Then the CAD data set is completed with the standard constructional data of the cone of the prosthesis neck for receiving the spherical head and of the implantation instrumentarium (drive-in/knock-out position of the prosthesis), and transferred to a milling unit. In the milling unit, the prosthesis component is milled from a blank, which is for example made of $V_4A$ steel. Upon a surface treatment, the prosthesis component is washed and sterilised and can then be inserted.

BRIEF DESCRIPTION OF THE DRAWINGS

In the following, the present invention is explained in more detail by means of the attached FIGURE. The FIGURE shows an embodiment of the prosthesis component according to the invention; cross-sections of the prosthesis as well as the inner and outer contour models of the femur are depicted in different sectional planes for further explanation.

DETAILED DESCRIPTION OF THE PREFERRED EMBODIMENTS

The FIGURE depicts a front view of the (implanted) prosthesis.

The prosthesis according to the FIGURE, which is schematically depicted in the femur, comprises an attachable spherical head 1 which sits on a cone 2 of the neck portion 3 of the prosthesis. Reference sign 4 designates the centre of rotation. The neck portion 3 is fixedly connected to a shaft 5 of the prosthesis. In the sectional planes which are approximately evenly distributed over the length of the proximal femur and in which the bone density per unit area is determined, the optimum shaft cross-sections 5' obtained as described above are drawn. Eight hatched shaft cross-sections 5' are drawn into the FIGURE and, for further clarification, three shaft cross-sections are additionally drawn at the side of the femur. Preferably, the bone density and the optimum shaft cross-section ensuing therefrom are determined in six to ten, for example nine sectional planes. Reference sign 6 designates the outer contour model and reference sign 7 the inner contour model of the femur in each of the sectional planes which are obtained by the image analysis. The mass and/or rigidity of the prosthesis in the individual sectional planes can be adjusted by designing the shaft cross-sections suitably. If, for example, the mass is to be low, the slot or recess in the U-shaped shaft cross-section is enlarged, wherein at the same time the largest possible surface for the transmission of forces between prosthesis and bone is provided in the medial portion of the prosthesis. If the specific mass in a sectional plane is changed, the rigidity of the prosthesis component in this portion also changes, as a rule. Reference sign 8 designates the constructional axis of the prosthesis which is at the same time the axis of the medullary canal and the implantation axis.

Literature:

Draenert K. (1988), Forschung und Fortbildung in der Chirurgie des Bewegungsapparates 2, zur Praxis der Zementverankerung, Munich, Art and Science.

Draenert K. and Draenert Y. (1992), Forschung und Fortbildung in der Chirurgie des Bewegungsapparates 3, die Adaptation des Knochens an die Deformation durch Implantate, Munich, Art and Science.

Noble PC, Alexander JW, Lindahl LJ, Yew DT, Granberry WM, Tullos HS, Clinical Orthopaedics and Related Research, No. 235, October 1988, pp. 148–163.

What is claimed is:

1. A method of producing a femoral prosthesis component for cement-free anchoring in the femoral portion near the hip joint, which component provides the largest possible surface for the transmission of forces and which component's mass and/or stiffness is adjustable to the individual properties of the femur, comprising the following process steps:

three-dimensionally reconstructing the medullary cavity of the femur from a series of sections;

producing a contour model of the femur with outer and inner contours;

determining the mean density of the bone in individual bone sections; and adapting the prosthesis to the medullary cavity of the femur using a correlation factor which correlates the mass and/or stiffness of the prosthesis with the mean bone density in the individual bone sections.

2. The method according to claim 1, wherein the mass and/or rigidity of the prosthesis is determined from the mean density of individual bone sections such that it is proportional to the bone density.

3. The method according to claim 1, wherein the sections are sections obtained by CT scan or sections obtained by nuclear spin tomography or histological sections.

4. The method according to claim 1, wherein, in the reconstruction of the medullary cavity, stacked images of the individual sections are digitized and electronically stored and subsequently processed to the contour model.

5. The method according to claim 1, wherein the shape of a shaft of the prosthesis is adapted to the shape of the medullary cavity.

6. The method according to claim 1, wherein the adapting step includes using the correlation factor to measure the strength of the bone sections, and wherein the correlation factor is used to determine the ratio of area between the cross-section of the prosthesis and the cross-section of the medullary cavity in each bone section.

7. The method according to claim 6, wherein the adapting step includes comparing the bone density per unit area, with the corresponding bone density per unit area of a normal femur, to determine the correlation factor of the strength of the bone for the determination of the ratio of area between the cross-section of the prosthesis and the cross-section of the medullary cavity.

8. The method according to claim 7, wherein the cross-section of the inner contour model is reduced according to the correlation factor by 1% to 20%, either eccentrically or concentrically or in turn eccentrically and concentrically along the constructional axis of the prosthesis.

9. The method according to claim 8, wherein the cross-section of the inner contour model is reduced according to the correlation factor by 5% to 10%.

10. The method according to claim 1, wherein the area of the cross-section of the prosthesis is between 30% and 90% of that of the cross-section of the medullary cavity.

11. The method according to claim 10, wherein the area of the cross-section of the prosthesis is between 40% to 80% of that of the cross-section of the medullary cavity.

12. The method according to claim 1, wherein the circumference of the cross-section of the prosthesis is constantly 70% to 95% of that of the inner contour of the medullary cavity.

13. The method according to claim 12, wherein the circumference of the cross-section of the prosthesis is constantly 80% to 90% of that of the inner contour of the medullary cavity.

14. The method according to claim 1, further comprising transmitting data of the contour model of the prosthesis to a CAD/CAM unit or a similar design system where they are processed in such a way that the contour model of the prosthesis is adapted to the contour model of the bone such that the prosthesis can be implanted along an implantation axis with a slight screwing movement.

15. The method according to claim 1, wherein the material of the prosthesis is selected from a group consisting of a CoCrMo alloy, titanium or a titanium alloy, steel or plastics or a composite material.

* * * * *

UNITED STATES PATENT AND TRADEMARK OFFICE
CERTIFICATE OF CORRECTION

PATENT NO. : 5,824,083

DATED : OCTOBER 20, 1998

INVENTOR(S) : KLAUS DRAENERT

It is certified that error appears in the above-identified patent and that said Letters Patent is hereby corrected as shown below:

On the Title Page, [30] Foreign Application Priority Data, delete "Apr. 24, 1993", insert --Apr. 24, 1992--

Signed and Sealed this

Fourteenth Day of September, 1999

Attest:

Q. TODD DICKINSON

*Attesting Officer*  *Acting Commissioner of Patents and Trademarks*